(12) United States Patent
Rosati et al.

(10) Patent No.: US 7,869,964 B2
(45) Date of Patent: Jan. 11, 2011

(54) METHOD FOR EVALUATION OF ABSORPTION BEHAVIOR OF ABSORBENT ARTICLES

(75) Inventors: Rodrigo Rosati, Frankfurt am Main (DE); Holger Beruda, Schwalbach (DE); Mattias Schmidt, Idstein (DE); Raffaele Virgilio, Brussels (BE); Bruno Johannes Ehrnsperger, Bad Soden (DE); Andrea Peri, Montesilvano (IT)

(73) Assignee: The Procter & Gamble Company, Cincinnati, OH (US)

( * ) Notice: Subject to any disclaimer, the term of this patent is extended or adjusted under 35 U.S.C. 154(b) by 167 days.

(21) Appl. No.: 12/248,379

(22) Filed: Oct. 9, 2008

(65) Prior Publication Data
US 2009/0099793 A1 Apr. 16, 2009

(30) Foreign Application Priority Data
Oct. 11, 2007 (EP) ................... 07118288

(51) Int. Cl.
*G06F 19/00* (2006.01)
(52) U.S. Cl. ..................................... 702/45
(58) Field of Classification Search ............ 702/45, 702/50
See application file for complete search history.

(56) References Cited

U.S. PATENT DOCUMENTS

| | | | |
|---|---|---|---|
| 4,773,904 A * | 9/1988 | Nakanishi et al. ........... 604/372 |
| 7,684,939 B2 * | 3/2010 | Allende-Blanco et al. ..... 702/50 |
| 2004/0014226 A1 | 1/2004 | Schrof et al. |
| 2004/0116888 A1 * | 6/2004 | Dorschner ............. 604/385.22 |
| 2004/0236455 A1 * | 11/2004 | Woltman et al. ............ 700/132 |
| 2004/0236456 A1 * | 11/2004 | Pieper et al. ................ 700/132 |
| 2005/0080391 A1 * | 4/2005 | Yoshimasa et al. ..... 604/385.01 |
| 2005/0222547 A1 | 10/2005 | Beruda et al. |
| 2005/0256686 A1 * | 11/2005 | Stabelfeldt et al. ............. 703/6 |
| 2007/0202772 A1 | 8/2007 | Ikeuchi et al. |
| 2008/0046202 A1 * | 2/2008 | Allende-Blanco et al. ..... 702/50 |
| 2008/0183450 A1 * | 7/2008 | Macura et al. ................. 703/9 |

FOREIGN PATENT DOCUMENTS

WO WO 2008/020411 A1 2/2008

OTHER PUBLICATIONS

International Search Report, dated Jan. 16, 2009, 7 pages.

* cited by examiner

*Primary Examiner*—Michael P Nghiem
*Assistant Examiner*—Cindy H Khuu
(74) *Attorney, Agent, or Firm*—John G. Powell; Kathleen Y. Carter (57) ABSTRACT

A method for designing an absorbent article and evaluating its absorption behaviour is disclosed. A system using the method, is also disclosed. The method may be used for analyzing movement of a fluid in an absorbent article that comprises fluid-swellable composite material, to determine the performance of at least one feature of the absorbent article. The method includes inputting one or more properties for said fluid-swellable composite material into a virtual model of the absorbent article to produce a representation of at least one feature of the absorbent article and evaluating the virtual model of the absorbent article to determine the performance of the feature.

18 Claims, 3 Drawing Sheets

METHOD FOR EVALUATION OF ABSORPTION BEHAVIOR OF ABSORBENT ARTICLES

FIELD OF THE INVENTION

The present invention relates to a method for designing an absorbent article, and in particular its absorption behaviour, using a specific model and a system using said model and a computer.

BACKGROUND OF THE INVENTION

Manufactures and developers of absorbent articles have traditionally relied upon results from physical testing of prototypes as a basis for evaluating the performance of absorbent articles and as a basis for making design changes. Developing prototypes of absorbent articles can be expensive because the equipment necessary to manufacture the absorbent article may not be developed at the time when new absorbent articles are being developed. In some instances, the materials from which the absorbent article will be constructed have yet to be developed. Furthermore, physical testing often requires working in a controlled laboratory environment, which can be expensive. In the case of hygienic products, such as catamenial devices, wound dressings, facial tissue, diapers, and diaper wipes, laboratory personnel may be exposed to increased risks to their health as a result of handling animal exudates during laboratory tests. For absorbent articles designed to absorb other materials, physical testing may require that laboratory personnel be exposed to unhealthy chemicals that the absorbent article is designed to absorb.

Obtaining data describing the transient behaviour of absorbent articles can be challenging. Often, a designer of absorbent articles is interested in how the absorbent article acquires fluid at the onset of exposure to a fluid. By the time the designer removes the absorbent article from exposure to the fluid, dissects the absorbent article, emplaces portions of the absorbent article and measures the distribution of the fluid therein, the distribution of the fluid can change significantly as compared to the distribution of fluid when the absorbent article was removed from contact with the fluid.

In some design processes for designing absorbent articles, physical testing on replicates of absorbent articles is needed to deduce conclusions based on observed results from testing. Testing replicates can help reduce uncertainties in making evaluations of different designs for absorbent articles and making decisions on how to improve designing of an article. Creating prototypes that are precise replicates of one another can be challenging, but when prototypes are not precise replicates of one another, interpreting testing results can be more difficult.

Absorbent articles are often designed to absorb a variety of substances. The substance may be a fluid containing only a single constituent, such as water. The substance may be a multi-phase fluid such as human menstrual fluid animal menses or bowel movement material. Physical testing of prototypes of absorbent articles exposed to substances comprising multiple components in multiple phases can be problematic, because the designer of the absorbent article may be unable to identify the particular impacts of specific phenomena on the performance of the absorbent article. Furthermore, the testing equipment used to test absorbent articles is often designed to test the absorbency with respect to clean water, rather than a substance containing a variety of solid, organic or inorganic fluid, and gaseous phases.

The fluid transport properties of absorbent materials commonly used in absorbent articles can be difficult to measure. Key fluid transport properties, which partially describe interactions between the absorbent and fluid, include the capillary pressure as a function of saturation and the relative permeability as function of saturation. Most commonly used methods for measuring the absorbent-fluid interaction properties are not suitable for testing with fluids other than water. Thus, there is a continuing unaddressed need for methods for developing absorbent articles that integrates physical measurements of the absorbent properties of absorbent materials into the design process. Additionally, there is a continuing unaddressed need for virtual product development methods that allow for the product developer to gather data on the transient performance of an absorbent article. Further, there is a continuing unaddressed need for methods for developing absorbent articles that do not rely entirely on physical testing of prototypes. There is also a continuing unaddressed need to be able to test absorbent materials and designs for absorbent articles without having to expose personnel to the substances absorbent articles are designed to absorb. Furthermore, there is a continuing unaddressed need for methods for measuring the capillary pressure versus saturation function for fluids other than water.

Co-pending U.S. application Ser. No. 11/504,993 filed on Aug. 16, 2006, now U.S. Pat. No. 7,684,939, describes a model and method to design articles with a certain fluid acquisition, solving the equation of continuity and partially saturated flow in porous media (also known as the Richard's equation). For absorbent articles that comprise fluid-swellable material (e.g., superabsorbent material or hydrogel-forming materials that absorb liquid due to an osmotic pressure gradients between the material and the surrounding fluid and that subsequently swell upon absorption), the traditional Richard's equation may no longer be sufficient to desirably describe the fluid flow through the swelling and/or swollen structure formed by the particles. In fact, the swelling process is an important factor because it can cause the structure to increase its thickness significantly, even (e.g.) 10 to up to 100 times. Such swelling may lead to changes of intrinsic properties such as permeability, capillary pressure and/or porosity. It is believed that such changes are controlled by the swelling kinetics of the water-swellable material in the product structure. Thus, there is a need for a design method to design absorbent articles comprising fluid-swellable composite material as mentioned above.

SUMMARY OF THE INVENTION

In order to provide a solution to the problems described above, at least one embodiment provides a method for analyzing movement of a fluid in an absorbent article that comprises fluid-swellable composite material, which comprises fluid-swellable solid material, to determine the performance of at least one feature of the absorbent article. The method also comprises inputting one or more properties for the fluid-swellable composite material or the fluid-swellable solid material into a virtual model of the absorbent article to produce a representation of at least one feature of the absorbent article. The method also comprises evaluating the virtual model of the absorbent article to determine the performance of the at least one feature of the absorbent article.

DETAILED DESCRIPTION

Disclosed herein is a method and system to evaluate the swelling of fluid-swellable composite materials and/or absorbent articles comprising said composite material and coupling it with the Richard's equation. The fluid-swellable composite material herein may comprise at least one fluid-swellable material in solid form, e.g., particles. In certain embodiments, the composite material comprises at least two such fluid-swellable materials, for example fluid-swellable particles and fluid-swellable fibres. In certain embodiments the fluid-swellable composite material additionally comprises non-fluid-swellable (solid) material. In certain embodiment the absorbent structure or article comprises said fluid-swellable composite material, which comprises fluid-swellable fibres and/ or at least fluid-swellable superabsorbent particles, and optionally also binders, adhesives, non-swellable fibres, and/or fillers.

"Fluid-swellable material" means a material or composite material that exhibits a change in volume (i.e., swelling) due to contact of the material or composite material with a fluid. Non-limiting examples of fluids that may cause a fluid-swellable material to swell include water, artificial menstrual fluid, blood, menstrual blood, human and animal menstrual fluid, synthetic vaginal discharge, human and menstrual vaginal discharge, synthetic urine, urine, fluid from a bowel movement, bowel movement analogue, sweat, synthetic sweat, skin care product, a lubricant, a surfactant, a cleanser, a detergent, a beverage, a petroleum product, and vomit, and mixtures thereof. In certain embodiments, the fluid-swellable material may absorb fluid, and then swell, due to an osmotic pressure gradient between the fluid in the material and the fluid outside the material. In certain embodiments, the fluid-swellable material may absorb fluid, and then swells due to the fact that the fluid changes one or more properties of the material, e.g., mechanical properties. While certain embodiments may describe fluid swelling materials, it is to be understood that materials that exhibit a decrease in volume when subjected to contact with a fluid are also contemplated herein. For example, the model may encompass embodiments that include fluff pulp fiber softening, fluff pulp fiber wet collapse, or decrease of volume of the fluid-swellable material due to external pressure and softening of the material.

The absorbent article herein may comprise fluid-swellable composite material and void space in said fluid-swellable composite material, e.g., between the fluid-swellable solid (particulate) material, e.g., such as the fluid-swellable superabsorbent material particles and fluid-swellable fibres. The absorbent article may be any article, but in one embodiment, the absorbent article is diaper, such as baby diapers, pull-on diapers, training pants, adult incontinence products (pads or diapers); or a feminine hygiene products, such as sanitary napkins and/ or panty-liners or tampons; or tissue paper; or wipes. The article may comprise said fluid-swellable composite material in a single absorbent region, layer (e.g., core), or in multiple regions or layers, and/or it may comprise regions or layers that temporarily absorb or distribute fluid, but do not swell (e.g., less than 20% volume increase, or preferably less than 10% or even less than 5%).

The virtual model herein may be a one dimensional model or a two or three dimensional model, The model herein uses certain assumptions/approximations, including, without limitation, the fluid-swellable composite material comprises fluid-swellable particulate material and may comprise voids between the particles of said material; liquid is either in said voids or inside the fluid-swellable particulate material; liquid movement is in one dimension only (e.g., x-direction); the fluid-swellable (composite) material swells only transverse (perpendicular) to the direction of liquid movement (swelling only in y or z direction); once liquid is inside the fluid-swellable material it remains inside; the liquid does not move inside the fluid-swellable material (e.g., liquid that enters the fluid-swellable material at point x will always stay at point x); liquid can distribute inside the voids, this distribution is governed by Darcy's law and liquid mass conservation; and/or the flow direction is horizontal, such that gravity can be neglected.

The model may however also be applied to a two dimensional or three dimensional situation. The (one dimensional) model equations herein is:

$$\frac{\partial m_1(x,t)}{\partial t} + \frac{\partial}{\partial x}\left(\begin{array}{l}D_1(m_1(x,t),m_2(x,t))\frac{\partial m_1}{\partial x} + \\ D_2(m_1(x,t),m_2(x,t))\frac{\partial m_2}{\partial x}\end{array}\right) == - \quad \text{(A1)}$$

$$f(S(m_1(x,t),m_2(x,t))\cdot \tau \cdot C_{AGM} \cdot A_0 \cdot \frac{m_{max}-m_2(x,t)}{m_{max}}$$

$$\frac{\partial m_2(x,t)}{\partial t} = +f(S(m_1(x,t),m_2(x,t))\cdot \tau \cdot C_{AGM} \cdot A_0 \cdot \frac{m_{max}-m_2(x,t)}{m_{max}} \quad \text{(A2)}$$

where:

x is the space dimension.

t is the time.

$m_1$ is the amount of liquid in voids per length.

$m_2$ is the amount of liquid in fluid-swellable material, e.g., particles, per length.

$$\frac{\partial f}{\partial t}$$

is the partial derivative of any variable $f(x,t)$ in respect to time t, e.g., $$\frac{\partial m_1}{\partial t}$$

is the partial derivative of $m_1$ in respect to time t.

$$\frac{\partial f}{\partial x}$$

is the partial derivative of any variable $f(x,t)$ in respect to space x, e.g., $$\frac{\partial m_1}{\partial x}$$

is the partial derivative of $m_1$ in respect to space x.

$D_1 = D_1(m_1(x, t), m_2(x, t))$ is the diffusivity 1 defined as $$D_1(m_1, m_2) = \rho_{liq} \cdot A(m_2) \cdot \frac{k(m_1, m_2)}{\mu} \cdot \frac{\partial P_c(m_1, m_2)}{\partial m_1}$$

$D_2 = D_2(m_1(x,t), m_2(x,t))$ is the diffusivity 2 defined as $$D_2(m_1, m_2) = \rho_{liq} \cdot A(m_2) \cdot \frac{k(m_1, m_2)}{\mu} \cdot \frac{\partial P_c(m_1, m_2)}{\partial m_2}.$$

$\rho_{liq}$ is the density of the liquid.

$A(m_2)$ is the cross section area. This is a function of $m_2$ and porosity (n). $A(m_2) = A(m_2(x,t), n(m_2))$. From volume conservation it is possible to express $A(m_2)$ as $$A(m_2) = \frac{(1 - n_{max})}{(1 - n(m_2(x, t)))} \cdot A_0 + \frac{m_2(x, t)}{\rho_{liq}}.$$

$k(m_1, m_2)$ is the permeability. This is in general a function of $m_1$ and $m_2$. (see the methods section below).

$P_c(m_1, m_2)$ is the capillary pressure. This is in general a function of $m_1$ and $m_2$. (see the method section below).

$\mu$ is the viscosity of the liquid—(see the method section below).

$$\frac{\partial P_c}{\partial m_1}$$

is the partial derivative of $P_c$ in respect to $m_1$.

$$\frac{\partial P_c}{\partial m_2}$$

is the partial derivative of $P_c$ in respect to $m_2$.

$\tau$ is the swelling speed (see the method section below). In general $\tau$ is a function of $m_2$.

$m_{max}$ is the maximum capacity (see method section below).

$$C_{AGM} = \frac{\text{Mass (dry fluid swellable material)}}{\text{Volume (dry fluid swellable material)}}$$

is the fluid-swellable material concentration, determined as ratio between mass and dry volume, where the mass is determined by weighing the fluid-swellable material, and the dry volume is calculated by determining caliper, length and width of the dry fluid-swellable composite material.

S is the liquid saturation in the voids and can be expressed as function of $m_1$ and $m_2$.

$$S(m_1, m_2) = \frac{m_1}{\rho_{liq} \cdot n(m_2) \cdot A(m_2)}.$$

$f(S(m_1(x,t), m_2(x,t)))$ is an empirical function expressing the dependency of the swelling kinetics on saturation in the voids. This function can be approximated with several equations, an example is to assume $f(S) = S$.

n is the porosity and is function of $m_2$. (see method section below).

$n_{max}$ is the value of porosity in dry conditions.

Figure 1:
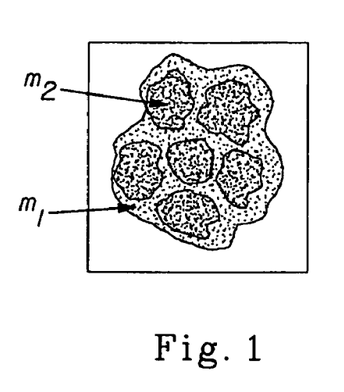
FIG. 1 shows an enlarged view of cross-sections of a fluid-swellable composite material with a number of water-swellable material particles with fluid in the pores between the particles and fluid in the particles (fluid between the solid parts of the composite material).

FIG. 1 exemplifies how the liquid in the material may be regarded as liquid in voids $m_1$ and liquid in fluid-swellable material, e.g., fluid-swellable material particles, $m_2$.

Equation (A1) and (A2) are the two coupled partial differential equations that determine the behaviour of liquid flow in the fluid-swellable composite material. Solving equations (1) and (2) means that values for $m_1$ (amount of liquid in voids per length) and $m_2$ (amount of liquid in fluid-swellable material, e.g., particles, per length) are obtained for all and/ or any times t and the whole or any space x. Solutions to equations (A1) and (A2) will depend on initial conditions and boundary conditions. An initial condition may, e.g., be that initially (at time t=t_0) there is no fluid in the voids and no fluid in the fluid swellable material, i.e., $m_1(t=t\_0, x) = 0$ and $m_2(t=t\_0, x) = 0$. A boundary condition may, e.g., be that fluid can neither enter nor leave the composite material at some boundary areas of the fluid swellable composite material, whilst at other boundary areas fluid is pressed into the fluid swellable composite material with a given pressure. Another boundary condition may be to keep the saturation (or the capillary pressure) at some area of the boundary constant. All the boundary conditions may be time dependent (i.e. change over time), and/or dependent on (time and/or space integrals over) $m_1$ and $m_2$.

Figure 2:
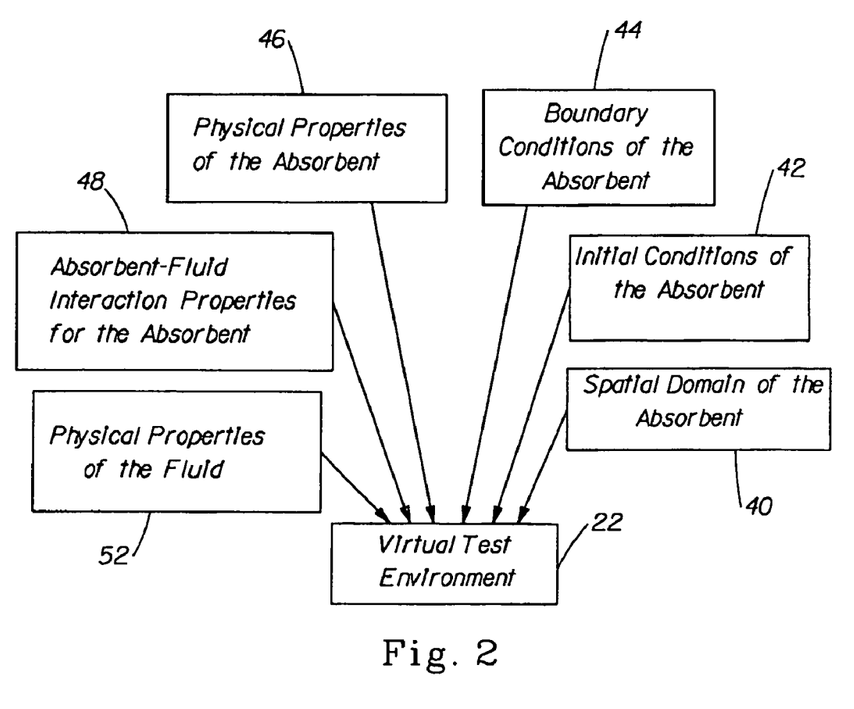
FIG. 2 is a schematic of a virtual test environment.

FIG. 2 is a schematic of the components of the virtual test environment 22. The virtual test environment includes the equations (A1) and (A2), in combination with a-v. The spatial domain of the absorbent region or layer (or core), e.g., layer 40, is specified and is divided into suitable volume elements, which together form what is commonly referred to as the mesh. The mesh may be coarse or fine, the choice of which may require consideration of the computing time for the virtual test environment 22 and the precision of results. A suitable coarseness or fineness may be determined by trial and error. Representative initial conditions of the absorbent core or layer 42 are also specified. The initial conditions of the absorbent 42 may be the same throughout the entire absorbent 44 or vary spatially. Initial saturation may be assumed to be zero, which is representative of an absorbent region or layer free of fluid. Alternatively, the absorbent in the virtual test environment 22 can be assumed to have an initial saturation that is not zero. A non-zero initial saturation can be representative of an absorbent that has absorbed fluid even in ambient conditions. Ambient conditions are the conditions of the absorbent prior to exposure to an insult of fluid. Representative boundary conditions of the absorbent 44 are prescribed for the virtual test environment 22. Boundary conditions can be for instance a given flux or a given constant saturation. An example of a boundary condition may be determined by a standard acquisition test with four 75 ml gushes and 5 minutes between the gushes, or 1 single gush of 10 ml. However any other test protocol can be herein described via properly formulating the boundary conditions.

Representative physical properties of the absorbent 46 include permeability, capillary pressure, swelling speed, maximum capacity, porosity, fluid-swellable composite material concentration. Representative absorbent-fluid interaction properties 48 for the absorbent may also be specified and include parameters of capillary pressure as function of saturation, relative permeability as function of saturation; they include all the dependencies of permeability, capillary pressure, swelling speed, maximum and porosity on $m_2$. Physical properties of the fluid 52 may also specified and include the fluid density and fluid viscosity.

The equations describing the virtual test environment 22 may be solved using direct methods, iterative methods, or any other methods known to those skilled in the art. The equations may, for example, be inputted into commercially available software. One example is to solve the equations (A1) and (A2) with general purpose solvers such as FORTRAN, gPROMS, or with commercial software, as for example FEFLOW, from Wasy GmbH, Walterdorfer Str. 105, 12526 Berlin Germany. The virtual model may also be performed iteratively by a software program developed in FORTRAN, C++, or similar programming language. Typically, the solver conditions and convergence criteria are specified. The start time, end time, maximum time-step, and initial time-step are also specified and put into the data set. The gravitational acceleration constant, reference temperature, and reference pressure may also be put into the solver data set. For some virtual test environments, the matrix of equations describing the virtual model may need to be preconditioned so that a solution meeting the specified convergence criteria is obtained. Trial and error may be used to determine if preconditioning is required. As part of the input, convergence criteria and stability parameters may be inputted to control the virtual test environment 22. The convergence criteria and stability parameters may be selected on a trial and error basis. As with most numerical solution approaches, there may be some trade-off between the criteria selected to control the virtual test environment 22 and the time required for solution and precision of results.

When FEFLOW is executed, FEFLOW creates output files as specified by the output controls. The output controls specify which time-steps output files are to be generated and what information is to be reported with each output file. Output from the virtual test environment 22 may comprise fluid saturation as a function of time and position. For each time-step for which output data is generated, the saturation S, the amount of liquid in fluid-swellable composite material $m_2$, and the capillary pressure for each cell can be reported. Hence the virtual test environment 22, may be used to generate a virtual spatial map of saturation as a function of location as a function of time.

Figure 3:
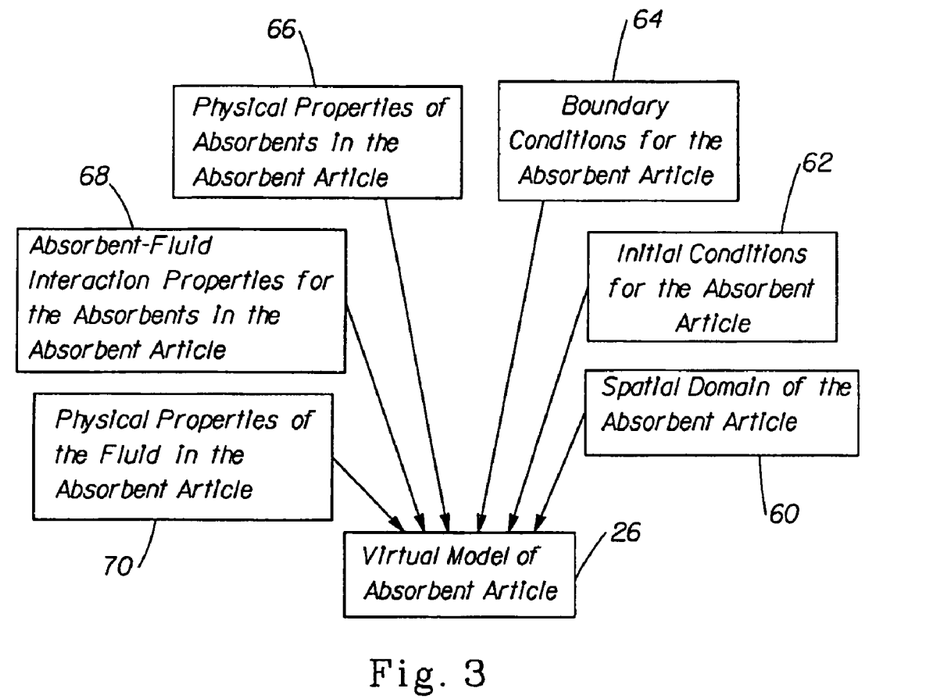
FIG. 3 is a schematic of a virtual test environment.

FIG. 3 is a schematic of the components of a virtual model of an absorbent article 26. To virtually model absorbent articles having complex shapes, the absorbent article can be conceptually divided into multiple volume elements. The volume elements, when assembled, form a mesh which can be referred to as the spatial domain of the absorbent article 60. The mesh may be created using any technique known to those skilled in the art including, but not limited to, conformal meshing, algebraic mesh generation schemes, and by solving partial differential equation schemes. For absorbent articles, the mesh may be uniform or non-uniform within a single layer structure. For symmetric absorbent articles, only a single section of the absorbent article may need to be virtually modelled. As with most numerical models, the user must weigh and consider the tradeoffs between the amount of computing time required, fineness of the mesh, and precision of results.

Representative initial conditions for the absorbent article 62 may also be specified. The initial conditions for the absorbent article 62 may be the same throughout the entire absorbent article or vary spatially. Initial saturation may be assumed to be zero, which is representative of an absorbent article free of fluid. Alternatively, the absorbent article in the virtual model of the absorbent article 26 may be assumed to have an initial saturation that is not zero. A non-zero initial saturation can be representative of an absorbent article that has absorbed fluid even in ambient conditions. Ambient conditions are the conditions of the absorbent article prior to exposure to an insult of fluid.

Representative boundary conditions of the absorbent article 64 may be prescribed for the virtual model of the absorbent article 26. Boundary conditions may be, for example, a given flux or a given constant saturation. An example of a boundary condition may be determined by a standard acquisition test with four 75 ml gushes and 5 minutes between the gushes, or 1 single gush of 10 ml. However any other test protocol may be herein described via properly formulating the boundary conditions.

Physical properties of the absorbents in the absorbent article 66 may also be specified for the virtual model of an absorbent article 26. The physical properties of the absorbents in the absorbent article 66 may be obtained from direct measurements of the properties, indirect measurements, inverse modelling, curve-fitting, material property databases, estimation, and/or any other method known to those skilled in the art. Physical properties of the fluid in the absorbent article 70 may also be specified and include the fluid density, fluid viscosity. Representative absorbent-fluid interaction properties 68 for the absorbents in the absorbent article may also be specified and include parameters of capillary pressure as function of saturation, relative permeability as function of saturation; they may include all the dependencies of permeability, capillary pressure, swelling speed, maximum capacity and porosity on m2.

Figure 4:
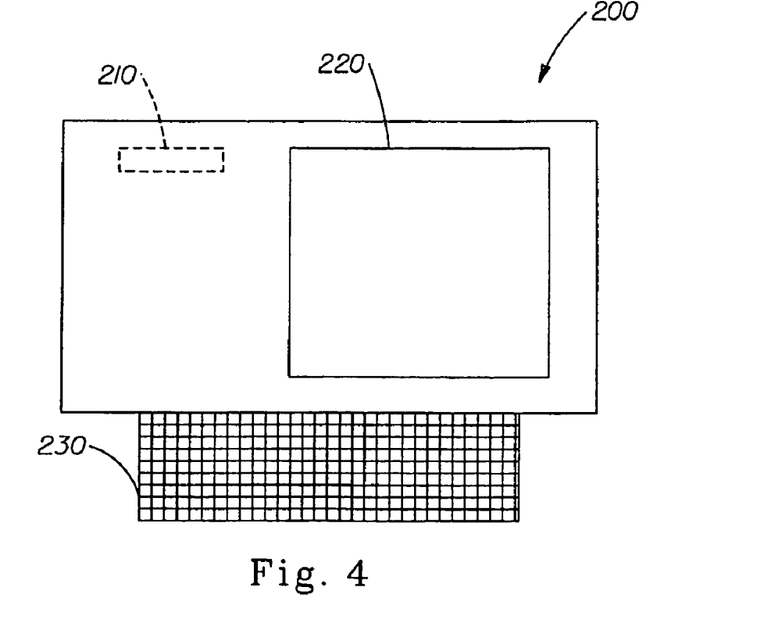
FIG. 4 is a block diagram illustrating one example of a computer system for operating the virtual test environment and operating the virtual absorbent article.

FIG. 4 is a block diagram illustrating one example of a computer system 200 for operating the virtual test environment 22 and the virtual model of an absorbent article 26. The computer system 200 comprises a central processing unit 210, a graphical user interface 220 including a display communicatively coupled to the central processing unit 210, and a user interface selection device 230 communicatively coupled to the central processing unit 210. The user interface selection device 230 may be used to input data and information into the central processing unit 210. The central processing unit 210 may include or have access to memory or data storage units, e.g., hard drive(s), compact disk(s), tape drive(s), and similar memory or data storage units for storing various data and inputs that may be accessed and used in operating the virtual test environment 22 and the virtual model of an absorbent article 26. Central processing unit 210 may be part of a SUN brand workstation running a UNIX brand operating system, part of a personal computer using INTEL PC brand architecture and running a MICROSOFT WINDOWS brand operating system, or part of another similarly capable computer architecture and accompanying operating system.

Methods (to Determine the Parameters Described Above)

The model herein is useful to predict the performance of the absorbent article or a structure thereof (herein referred to as (absorbent) region, layer or core) comprising the fluid-swellable composite material, while only needing to obtain only certain fluid-swellable composite material properties such as:
1) Porosity (n).
2) Swelling Speed ($\tau$):
3) Maximum Capacity ($m_{max}$)
4) Permeability (k);
5) Capillary pressure ($p_c$):

It is known to one skilled in the art, that all of the properties above may depend on the confining pressure applied onto the sample during the measurement; this can change from 0 up to 1-2 psi, i.e. to mimic a range of very different usage conditions, e.g., the user just walking and exerting only a slight pressure on the article or the user sitting on the article, hence exerting a certain pressure on the article. Therefore the description below should be intended to be applicable to any pressure.

Porosity (n)

Porosity of the fluid-swellable (composite) material may be obtained from the capillary pressure versus saturation function (or data), computed using mass/volume/density relationships, measured using a column test, determined from image interpretation, or any other method known to those skilled in the art. By repeating the measurements with liquids with different salt concentration, ranging for instance from 0.5 to 25% of NaCl by weight, porosity data can be determined as function of fluid-swellable composite material load (different salt concentration would induce a different swelling extent). Data of porosity as function of fluid-swellable composite material load may then be fitted with any convenient mathematical dependency.

An example is a linear correlation;

$$n(m_2) = A + B \cdot U(m_2)$$

Dependence of fluid-swellable composite material load U on $m_2$ is given by:

$$U(m_2) = \frac{m_2}{C_{AGM} \cdot A_0}$$

In the equation above A and B are fitting parameters, to be determined with fitting methods, known in the art.

Swelling Speed ($\tau$) and Maximum Capacity ($m_{max}$)

Swelling speed $\tau$ and maximum capacity are properties that may be dependent on the type of fluid-swellable (composite) material used, the external pressure, temperature, and the liquid type used. In general, $\tau$ is a function of $m_2$, but in some embodiments it may be assumed to be constant, such as shown herein. Then, for fluid-swellable composite material that is totally surrounded with liquid, the equation (A2) reduces to:

$$\frac{\partial m_2(x,t)}{\partial t} = \tau \cdot C_{AGM} \cdot A_0 \cdot \frac{m_{max} - m_2(x,t)}{m_{max}} \quad (A3)$$

Integration of (A3) with no liquid ($m_2=0$) in the fluid-swellable (composite) material at t=0 results in:

$$m_2(t) = m_{max} \cdot \left(1 - e^{-\frac{\tau \cdot C_{AGM} \cdot A_0 \cdot t}{m_{max}}}\right) \quad (A4)$$

Therefore, any method able to measure uptake as function of time can be used to generate the experimental data, which is then to be fitted with equation (A4). For instance, the method as described below in the "capillary pressure section", can be executed with air pressure equal to atmospheric pressure, where the absorbent material will be fully loaded. The recorded "uptake versus time" data is then used with equation (A4), getting the unknown parameters swelling speed ($\tau$) and max capacity ($m_{max}$).

Permeability (k)

Permeability for a fluid-swellable (composite) material is a function of $m_2$ and $m_1$, where $m_2$ and $m_1$ are as defined above.

$$k = f(m_1, m_2) = k_0(m_2) \cdot k_r(m_1, m_2)$$

where
$k_0$ is the saturated permeability
$k_r$ is the relative permeability, defined as $$k_r = \frac{k_{S*}}{k_0}$$

where $k_{S*}$ is the permeability at a particular S* and $k_0$ is the intrinsic permeability (e.g., saturated permeability).

This is described in more detail in the literature on the dependency of the permeability on the swelling extent of the porous media, e.g., Model of Liquid Permeability in Swollen Composites of Superabsorbent Polymer and Fiber, Fredric L. Buchholz Dow Chemical Company, Journal of Applied Polymer Science, Vol. 102, 4075-4084 (2006). This complex dependency may be handled in a model by assuming that the dependence of permeability on $m_1$ and $m_2$ can be factored into a dependence on fluid-swellable composite material load U and saturation S as follows:

$$k(m_1, m_2) = k_0(U) \cdot S^b = k_0(U(m_2)) \cdot S(m_1, m_2)^b \quad (A5)$$

Dependence of fluid-swellable (composite) material load U on $m_2$ is given by:

$$U(m_2) = \frac{m_2}{C_{AGM} \cdot A_0}$$

Generally, the saturated permeability $k_0$ of an absorbent may be directly measured in the laboratory. The in-plane and thru-plane saturated permeability may be measured using any means known to those skilled in the art including, but not limited to, constant hydrostatic pressure head method, and constant volume flow rate method. The saturated absorbent can be subjected to a constant hydrostatic pressure head from a column of fluid about 1 to about 100 cm in height. The column height range may be from about 5 to about 50 cm. The material may be held in place by the hydrostatic pressure head of the fluid or with additional confining pressure. The mass flow rate of fluid through the absorbent layer or core is recorded for a set period of time. The mass flow rate is used to calculate the saturated permeability of the absorbent, knowing the area of the absorbent orthogonal to the direction of flow, the thickness of the absorbent in a direction in-plane with the direction of flow, and the change in total pressure head across the absorbent. $k_0$ as function of U may be obtained by modifying any of the methods above as follows. Instead of using a standard liquid having a standard salt concentration, liquids with different salt concentrations (e.g., ranging for instance from 0.5 to 25% of NaCl by weight) may be used (a different salt concentration would induce a different swelling extent U) and then permeability at a specific load U may be measured. The specific load U corresponding to a certain salt concentration may be measured as in the porosity method described herein.

In the formula (A5) above, the relative permeability is described through a power model, where the coefficient b may be estimated based on the literature value or calculated with inverse fitting. A typical value for b may range between 3 and 5. Another suitable example of a model used to describe relative permeability includes, without limitation the van Genuchten-Mualem model (see van Genuchten, M. T. (1980), "A Closed-Form Equation for Predicting the Hydraulic Conductivity of Unsaturated Soils," *Soil Science Society of America*, 44, 892-898 and Mualem, Y. (1976), "A New Model for Predicting the Hydraulic Conductivity of Unsaturated Porous Media," *Water Resources Research*, 12(3), 513-522)). The van Genuchten-Mualem model for relative permeability is:

$$k_r = \sqrt{S^*}\left[1 - \left(1 - [S^*]^{\frac{1}{\lambda}}\right)^{\lambda}\right]^2$$

where $\lambda$ is a fitting parameter that is partially descriptive of the shape of the relative permeability function. The parameter $\lambda$ is then also one of the absorbent-fluid interaction properties 48 for the absorbent.

Capillary Pressure ($P_c$)

Capillary pressure for a fluid swellable (composite) material is herein given as a complex function of $m_2$ and $m_1$.

$$p_c = f(m_1, m_2)$$

To handle this complex dependency in a model, it may be assumed that the capillary pressure only depends on the liquid saturation S in the voids around the fluid-swellable composite material (i.e., $P_c(m_1, m_2) = P_c(S)$). This dependence is parameterized according to Van Genuchten (M. T Van Genuchten, "A closed-form equation for predicting the hydraulic conductivity of unsaturated soils." Soil Sci. Soc. Am. J. 44, pp. 892-898, (1980)):

$$p_c(S(m_1, m_2)) = \overline{P} \cdot ^{nabs}\sqrt{S(m_1, m_2)^{\frac{nabs}{1-nabs}} - 1} \quad (A6)$$

with:

$$S(m_1, m_2) = \frac{m_1}{\rho_{liq} \cdot n(m_2) \cdot A(m_2)}$$

The parameters nabs and $\overline{P}$ in equation (A6) can be determined from fitting experimental capillary pressure curves, including both uptake and retention curves; different parameters nabs and $\overline{P}$ will be determined for the uptake and retention branches of the hysteresis curves. Various test methods are available to measure and estimate capillary pressure curves of a porous media, e.g., from Absorbent Technology, edited by P. K. Chatterjee and B. S. Gupta, Elsevier, page 426-436 or Liquid Porosimetry: New Methodology and Applications, Miller and Tyomkin, Journal of Colloid and Interface Science, 162, p 163-170 (1994).

Figure 5:
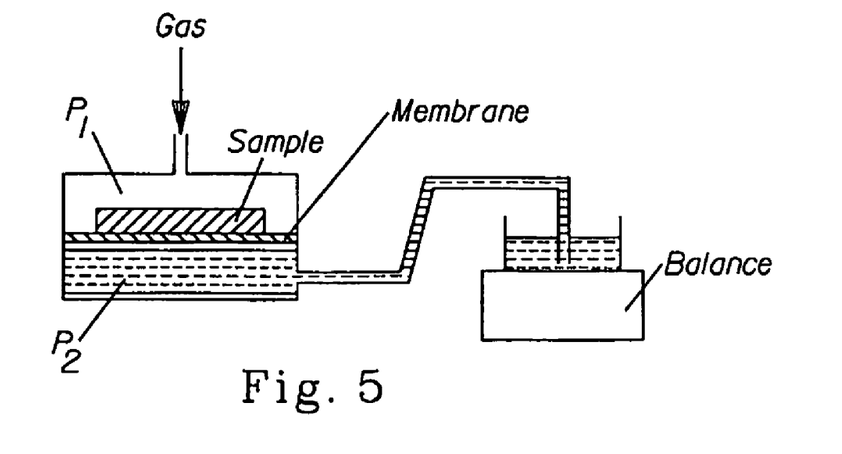
FIG. 5 shows equipment used to determine the capillary pressure, used herein

FIG. 5 represents a schematic of a typical method used to measure capillary pressure curves of porous media. The presaturated specimen is placed on a microporous membrane which is itself supported by a rigid porous plate (the presaturated specimen may be obtained by any method, e.g., placing a dry sample onto the membrane and decreasing the chamber gas pressure to the atmospheric pressure and allowing the liquid to enter into all the pores of the material). The gas pressure within the chamber is increased in steps, causing liquid to flow out of some of the pores, typically out of the largest pores first. The amount of liquid removed may be monitored by a top-loading recording balance. In this way each level of applied pressure (which determines the largest effective pore size that remains filled) is related to an increment of liquid mass. Stepwise drainage from large pores may require very small increases in pressure over a narrow range that is only slightly above atmospheric pressure. For drainage from small pores, the pressure changes may be quite large. Accordingly, the chamber is pressurized by means of a computer controlled, reversible, motor driven piston/cylinder arrangement that can produce the required changes in pressure to cover a pore radius range from 1 to 1000 micron. It is also possible to measure the uptake curve for a dry sample; in this case the air pressure will be decreased step-wise. This method may also be applied to a fluid-swellable (composite) material itself that is pre-swollen to full load (e.g., by leaving the specimen under atmospheric pressure for at least 2 hours in the test liquid), by then increasing the outside air pressure and measuring the retention curve, and then decreasing this again to measure the uptake curve.

The parameters nabs and $\overline{P}$ in equation (4) may also be obtained from functions of the fluid-swellable composite material load: this would require the capillary pressure measurements above to be performed with liquids having different salt concentration, as explained in the permeability section.

Figure 6:
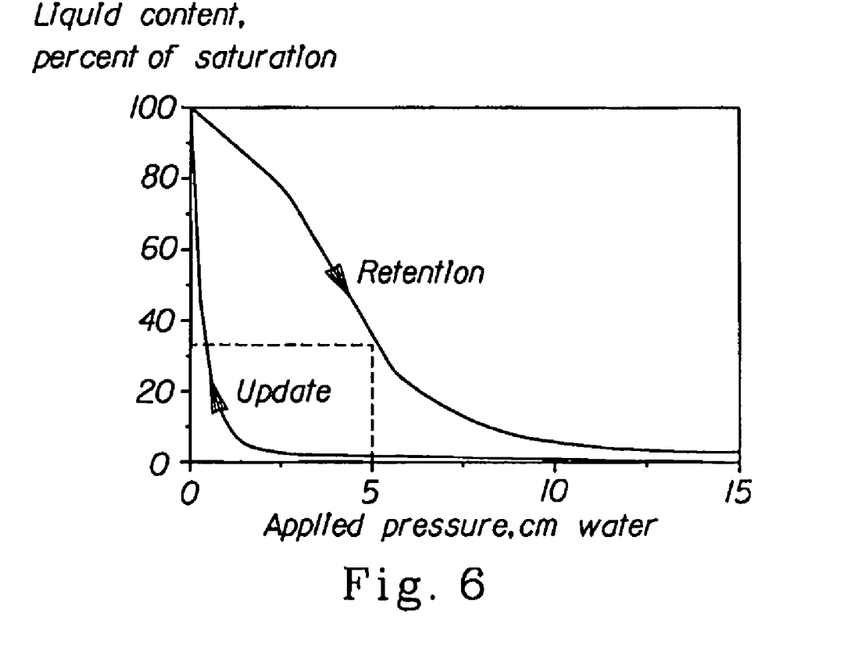
FIG. 6 shows typical capillary pressure curves obtained with the equipment of FIG. 5.

FIG. 6 shows typical capillary pressure curves as measured with the method above with the test equipment shown in FIG. 5. The capillary pressure for a specific liquid of known contact angle and surface tension may also be obtained from the measured capillary pressure of a second liquid of known contact angle and surface tension.

Viscosity

Viscosity can be determined with any suitable viscosity method known in the art, e.g., ISO/TR 3666:1998 or DIN 53018-1:1976.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for analyzing movement of a fluid in an absorbent article that comprises fluid-swellable composite material, which comprises a fluid-swellable solid material, to determine the performance of at least one feature of the absorbent article, said method comprising:

inputting one or more properties for said fluid-swellable composite material or fluid-swellable solid material thereof into a virtual model of the absorbent article to produce a representation of at least one feature of the absorbent article; and evaluating, using a computer, the virtual model of the absorbent article to determine the performance and of the at least one feature of the absorbent article, wherein the virtual model comprises a solution to the equations $$\frac{\partial m_1(x,t)}{\partial t} + \frac{\partial}{\partial x}\left(D_1(m_1(x,t), m_2(x,t))\frac{\partial m_1}{\partial x} + D_2(m_1(x,t), m_2(x,t))\frac{\partial m_2}{\partial x}\right) = \tag{1}$$

$$-f(S(m_1(x,t), m_2(x,t)) \cdot \tau \cdot C_{AGM} \cdot A_0 \cdot \frac{m_{max} - m_2(x,t)}{m_{max}}$$

and $$\frac{\partial m_2(x,t)}{\partial t} = +f(S(m_1(x,t), m_2(x,t)) \cdot \tau \cdot C_{AGM} \cdot A_0 \cdot \frac{m_{max} - m_2(x,t)}{m_{max}},$$

and wherein the solutions are used to develop, an absorbent article.

2. The method according to claim 1, wherein the properties are selected from the group consisting of Concentration of the fluid-swellable material, Porosity, Swelling Speed, Maximum Capacity, Capillary Pressure and Permeability.

3. The method according to claim 1, wherein the fluid-swellable composite material includes void spaces, and the performance being evaluated includes at least one of an amount of liquid absorbed by the fluid-swellable composite material, an amount of liquid present in the void spaces, and a thickness of the fluid-swellable composite material.

4. The method according to claim 3, wherein the amount of liquid absorbed by the fluid-swellable composite material is determined for at least one of a certain time and a certain space in the absorbent article.

5. The method according to claim 3, wherein the amount of liquid present in the void spaces is determined for at least one of a certain time and a certain space in the absorbent article.

6. The method according to claim 1, wherein the virtual model relates to the movement of a fluid in the absorbent article in a first dimension and swelling of the fluid-swellable composite material in a dimension perpendicular to the first dimension.

7. The method as in claim 6, wherein at least one of the movement of fluid and the swelling of the fluid-swellable composite material is in two dimensions or three dimensions.

8. The method according to claim 1, wherein the fluid is selected from the group consisting of water, artificial menstrual fluid, blood, menstrual blood, human and animal menstrual fluid, synthetic vaginal discharge, human and animal vaginal discharge, synthetic urine, urine, fluid from a bowel movement, bowel movement analogue, sweat, synthetic sweat, a skin care product, a lubricant, a surfactant, a cleanser, a detergent, a beverage, a petroleum product, and mixtures thereof.

9. The method according to claim 1, wherein the absorbent article is selected from the group consisting of diapers, training-pants, adult incontinence products; sanitary napkins, panty liners; wipes; tissues; breast pads, paper towels, toilet paper, wound dressings, and handkerchiefs.

10. A system for analyzing movement of fluid in an absorbent article, which includes fluid-swellable composite material comprising fluid-swellable solid material said system comprising:

a computer that includes a central processing unit, a graphical user interface comprising a display communicatively coupled to said central processing unit, and a user interface selection device communicatively coupled to said central processing unit; the computer further including a computer-based virtual model of the absorbent article configured to produce a representation of the at least one feature of the absorbent article based on inputting one or more properties of the fluid-swellable composite material or the fluid-swellable solid material; and a computer readable memory device containing data and instructions for evaluating the virtual model to determine the performance of a feature of the absorbent article, wherein the virtual model comprises a solution to the equations:

$$\frac{\partial m_1(x,t)}{\partial t} + \frac{\partial}{\partial x}\left(\begin{array}{c}D_1(m_1(x,t), m_2(x,t))\frac{\partial m_1}{\partial x} + \\ D_2(m_1(x,t), m_2(x,t))\frac{\partial m_2}{\partial x}\end{array}\right) == - \tag{1}$$

$$f(S(m_1(x,t), m_2(x,t)) \cdot \tau \cdot C_{AGM} \cdot A_0 \cdot \frac{m_{max} - m_2(x,t)}{m_{max}} \text{ and}$$

$$\frac{\partial m_2(x,t)}{\partial t} = +f(S(m_1(x,t), m_2(x,t)) \cdot \tau \cdot C_{AGM} \cdot A_0 \cdot \frac{m_{max} - m_2(x,t)}{m_{max}}.$$

11. The system according to claim 10, wherein the properties are selected from the group consisting of Concentration of the fluid-swellable composite material, Porosity, Swelling Speed, Maximum Capacity, Capillary Pressure, Permeability, and combinations thereof.

12. The system according to claim 11, wherein initial and boundary conditions are inputted.

13. The system according to claim 10, wherein the performance being evaluated is selected from the group consisting of an amount of liquid absorbed by said fluid-swellable composite material and the amount of liquid present in said void spaces.

14. The system of claim 13, wherein the performance being evaluated is evaluated as a function of at least one of time and position in the absorbent article.

15. The system according to claim 10, wherein the virtual model analyzes movement of a fluid in an absorbent article in a first dimension and swelling of said fluid-swellable composite material in another dimension, perpendicular to said first dimension.

16. The system according to claim 10, wherein the fluid used is selected from the group consisting of artificial menstrual fluid, menstrual fluid, synthetic vaginal discharge, vaginal discharge, synthetic urine, urine, fluid from a bowel movement, bowel movement analogue, sweat, synthetic sweat, skin care product, a lubricant, a surfactant, a cleanser, a detergent, a beverage, a petroleum product, and vomit.

17. The system according to claim 10, wherein the absorbent article is selected from the group consisting of diapers, including baby diapers, training-pants, incontinence products; feminine hygiene articles, including pads, napkins; wipes; tissues, including breast pads, paper towels, toilet paper, wound dressings, handkerchiefs, household wipes.

18. The system according to claim 10, wherein the fluid-swellable composite material comprises non-swellable material.

* * * * *

UNITED STATES PATENT AND TRADEMARK OFFICE
CERTIFICATE OF CORRECTION

| | | |
|---|---|---|
| PATENT NO. | : 7,869,964 B2 | Page 1 of 1 |
| APPLICATION NO. | : 12/248379 | |
| DATED | : January 11, 2011 | |
| INVENTOR(S) | : Rosati et al. | |

It is certified that error appears in the above-identified patent and that said Letters Patent is hereby corrected as shown below:

Column 4

Line 7, after the words dimensional model, delete the "," and insert a --.--.

Column 8

Line 30, delete "article 26" and insert --article 66--.

Signed and Sealed this
Sixth Day of December, 2011

David J. Kappos
*Director of the United States Patent and Trademark Office*